US007112180B2

(12) United States Patent
Guenther

(10) Patent No.: US 7,112,180 B2
(45) Date of Patent: Sep. 26, 2006

(54) BELOW-KNEE ORTHOTIC DEVICE

(75) Inventor: Norbert Guenther, Parsdorf (DE)

(73) Assignee: F. Gottinger Orthopaedie-Technik GmbH, Zorneding (DE)

( * ) Notice: Subject to any disclaimer, the term of this patent is extended or adjusted under 35 U.S.C. 154(b) by 49 days.

(21) Appl. No.: 10/478,650

(22) PCT Filed: Apr. 23, 2002

(86) PCT No.: PCT/DE02/01486

§ 371 (c)(1),
(2), (4) Date: Dec. 1, 2003

(87) PCT Pub. No.: WO02/096328

PCT Pub. Date: Dec. 5, 2002

(65) Prior Publication Data

US 2004/0186401 A1   Sep. 23, 2004

(30) Foreign Application Priority Data

May 31, 2001   (DE) .................................. 101 26 622

(51) Int. Cl.
*A61F 5/00*   (2006.01)
(52) U.S. Cl. ............................ 602/23; 602/27; 602/28; 602/29; 602/65; 128/882
(58) Field of Classification Search ................... 602/16, 602/23, 27–29, 62, 65; 128/882, 869; 2/22; 16/374–375; 36/140
See application file for complete search history.

(56) References Cited

U.S. PATENT DOCUMENTS

| 2,525,237 | A | * | 10/1950 | Park | 602/28 |
|---|---|---|---|---|---|
| 2,557,603 | A | * | 6/1951 | Invidiato | 602/28 |
| 2,663,294 | A | * | 12/1953 | Harrison | 602/28 |
| 3,827,430 | A |  | 8/1974 | Fadden |  |
| 4,919,118 | A | * | 4/1990 | Morris | 602/16 |
| 5,022,390 | A | * | 6/1991 | Whiteside | 607/2 |
| 5,144,943 | A | * | 9/1992 | Luttrell et al. | 601/34 |
| 5,328,444 | A | * | 7/1994 | Whiteside | 602/16 |
| 5,382,224 | A | * | 1/1995 | Spangler | 602/23 |
| 5,431,624 | A | * | 7/1995 | Saxton et al. | 602/27 |
| 5,609,570 | A |  | 3/1997 | Lamont |  |
| 5,716,336 | A | * | 2/1998 | Hines et al. | 602/27 |
| 5,897,514 | A | * | 4/1999 | Currier | 602/16 |
| 5,944,679 | A |  | 8/1999 | DeToro |  |
| 6,171,272 | B1 | * | 1/2001 | Akita et al. | 602/28 |
| 6,491,654 | B1 | * | 12/2002 | Lamont | 602/13 |
| 6,824,523 | B1 | * | 11/2004 | Carlson | 602/16 |
| 2004/0260220 | A1 | * | 12/2004 | Wagner et al. | 602/16 |

FOREIGN PATENT DOCUMENTS

DE   196 04 309 A1   8/1997
DE   299 08 981 U 1   1/2000

OTHER PUBLICATIONS

PTO 05-4453: Translation of DE 29908981 "Lower Leg Orthosis", Jun. 2005, FLS, Inc.*

* cited by examiner

*Primary Examiner*—Henry Bennett
*Assistant Examiner*—Amanda Wieker
(74) *Attorney, Agent, or Firm*—Oliff & Berridge, PLC.

(57) ABSTRACT

A below-knee orthotic device in which dorsal flexion and plantar flexion are enabled by a support spring connecting a lower leg sleeve and a foot sleeve. The support spring is clamped in the foot sleeve, so that a gap is formed between the heel part and the foot sleeve, wherein bending of the support spring in stepping direction is limited through a stop on the foot sleeve.

14 Claims, 7 Drawing Sheets

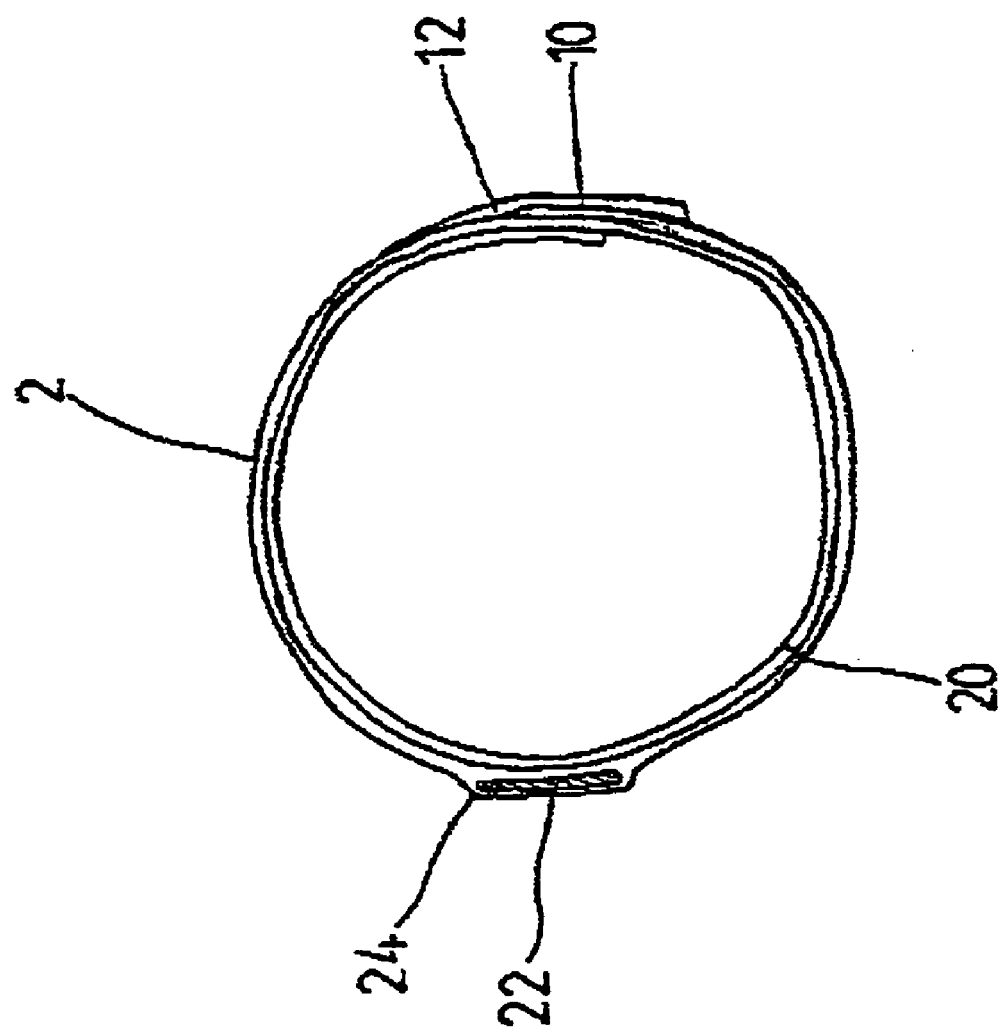

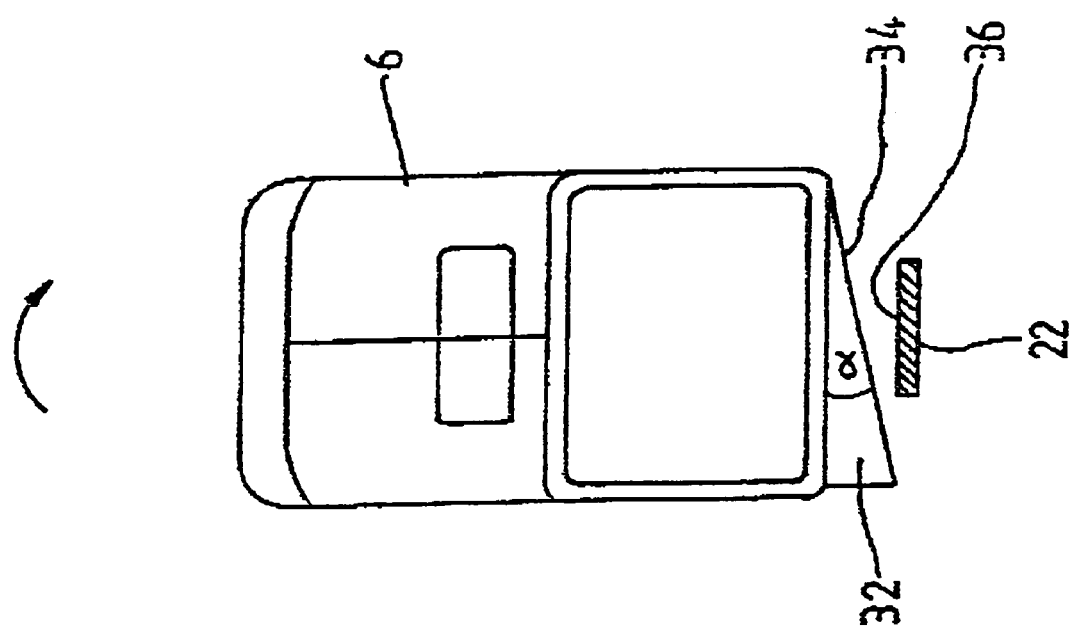

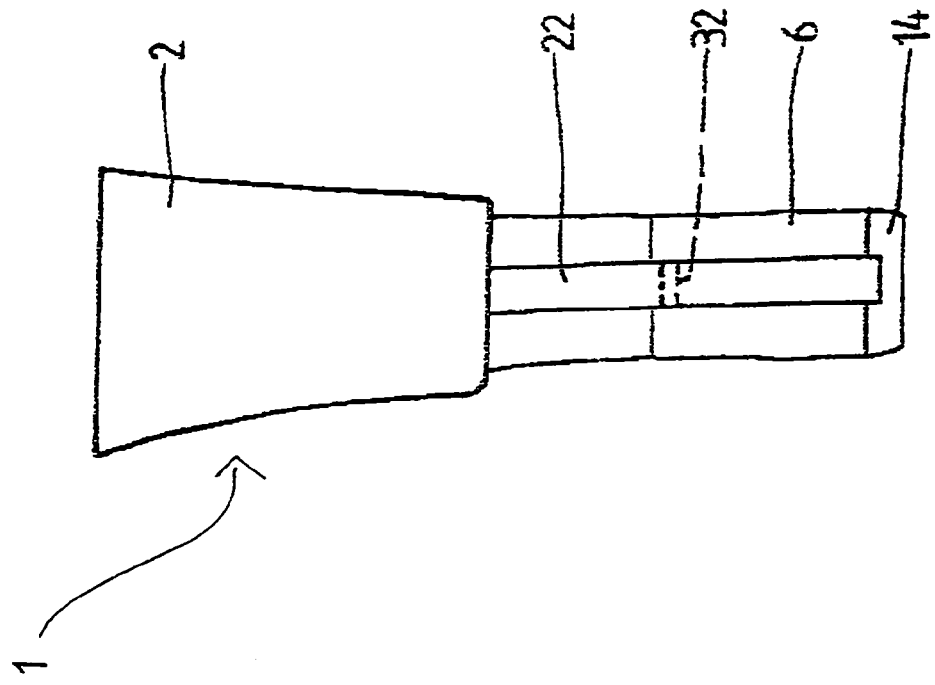
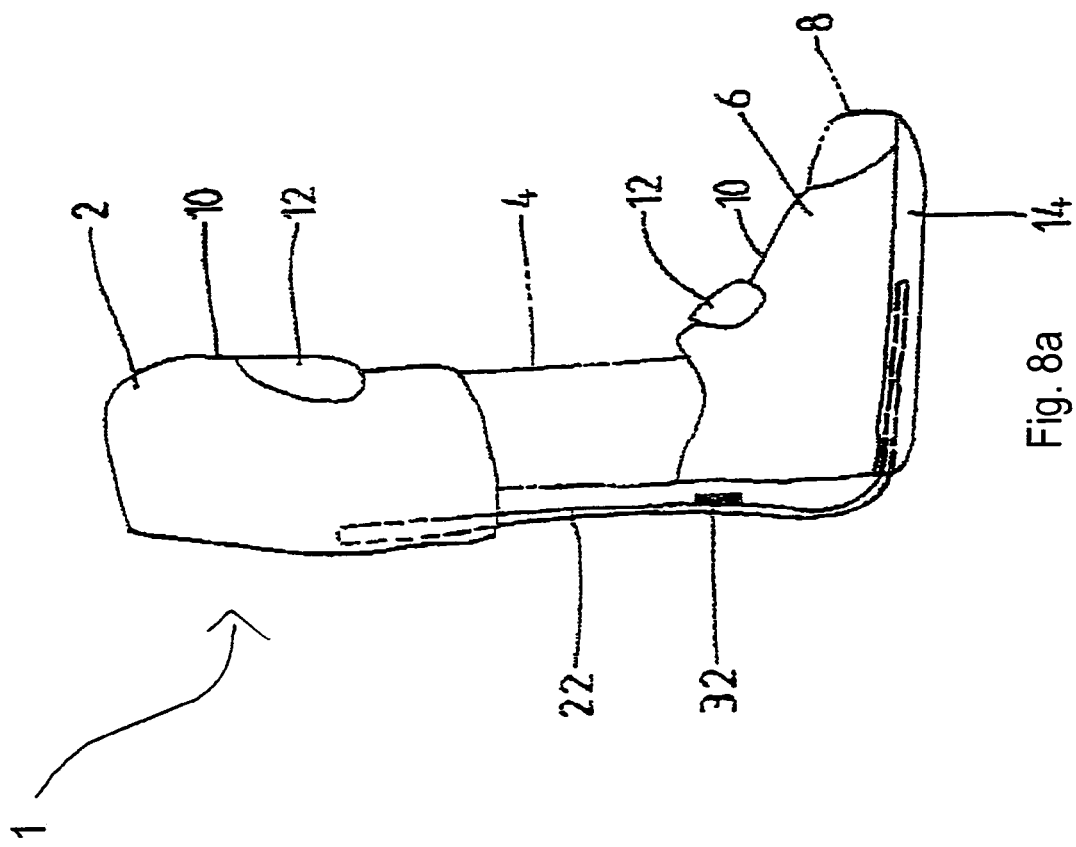

BELOW-KNEE ORTHOTIC DEVICE

BACKGROUND

The disclosure relates to a below-knee orthotic device and a support spring provided therefor.

The like orthotic devices are used, for instance, for patients afflicted with a deep paralysis, in muscular disorders, infantile cerebral pareses, pathological disorders, neurological changes, or also with healthy persons in order to support the function of the human foot. By the orthotic device, the foot is contained relative to the lower leg while determinably releasing a forward and backward movement, i.e., movement in the longitudinal direction. Forward mobility here is generally established over a larger range than rearward mobility. Relative mobility of the foot in a transverse direction relative to the lower leg is to be reduced to a minimum in most cases.

Previously utilized orthotic devices include a foot sleeve and a lower leg sleeve connected to each other through ankle joints of metal. It is a drawback in this construction that the ankle joints are subjected to a considerable strain and thus to a considerable wear, and therefore need to be of a comparatively sturdy design. Freedom of movement is predetermined by stops formed in the ankle joint.

Owing to the comparatively sturdy design of the ankle joints, these known orthotic devices have a considerable weight which restricts patients' mobility. It is another drawback that sturdy ankle joints require considerable construction space, with the orthotic device accordingly conveying a rather awkward impression.

In accordance with utility model 29908981.9, a below-knee orthotic device including a support spring in a lower leg sleeve and foot sleeve formed in a single piece is known, with an articulation slot being formed in the transitory range.

It is, however, a disadvantage in this utility model that, due to the integral design, slight pendulum motions of the patient bring about unintended initiation of a step, resulting in considerable problems of equilibrium.

SUMMARY

The below-knee orthotic device 1 envelops with a lower leg sleeve 2 and the lower leg 4 (indicated in triple dots); and with a foot sleeve 6 and the foot 8 (double dots) of the patient, these sleeves being connected to each other through a support spring 22 controlling the movement.

It is an object of the invention to furnish a below-knee orthotic device and a support spring whereby sufficient mobility and stability are ensured with minimum expenditure in terms of device technology.

According to the invention, the below-knee orthotic device has at least one support spring whereby a height-adjustable lower leg sleeve and a foot sleeve are connected to each other. This support spring is designed such that it releases mobility in the longitudinal direction (lifting the foot, lowering the foot) in the required range. The support spring may be designed such that mobility in the transverse direction is minimum (stiff), or such that an intentional flexibility is admitted in order to allow for an intentional counter-rotation and steering.

The support spring stores potential energy in the movement, e.g. upon angular flexure of the foot, so that the dorsal flexion during the momentum phase is enabled and supported by the release of the support spring. In this way, energy-saving walking with an expenditure of force reduced in comparison with conventional solutions is possible.

The support spring moreover permits walking up-and downhill by shifting the point of gravity.

In a particularly preferred embodiment, the support spring has the form of an approximately L-shaped leaf spring, designed to have in the heel range preferably two inversely curved portions which continue into end portions on the side of the foot and on the side of the lower leg. The leaf spring extends along the rear side of the lower leg over the heel and along a part of the sole of the foot sleeve. The support spring may be accommodated in provided receptions or embedded in the sleeve material.

The leaf spring is guided in the foot sleeve so that it is only connected on its foot-side end portion with the foot sleeve, with a resulting gap between the rear face of the foot sleeve and the heel part, or the part of the leaf spring on the side of the lower leg. With the aid of a defined stop on the rear side of the foot sleeve, the relative movement of the foot sleeve relative to the heel part of the support spring is limited upon initiation of a step.

In order to give some patients greater freedom of movement through rotation of the support spring about the vertical longitudinal axis, e.g. by reducing the support spring width in the middle portion (heel part), and yet guide the foot in a manner that is optimal for the patients upon initiation of a step, one embodiment provides a preferably wedge-shaped design of the stop.

One alternative for the wedge-shaped stop is an engagement means on the level of the heel part, where e.g. a wedge engages a groove in the support spring.

A below-knee orthotic device having particularly high stability and low weight is obtained when the support spring is manufactured of fiber reinforced plastic, preferably of carbon fiber.

Other advantageous developments of the invention are subject matters of the further subclaims.

BRIEF DESCRIPTION OF THE DRAWINGS

In the following, a preferred embodiment of the invention is explained in more detail by reference to schematic drawings, wherein:

FIG. 2 is a cross-sectional view along lines 2—2 in FIG. 1;

FIG. 6 is a simplified top view of a stop having a wedge-shape;

FIGS. 8a–8b are a simplified representation of the below-knee orthotic device of FIG. 1 in lateral and rear view with a stop disposed on a support spring.

DETAILED DESCRIPTION OF PREFERRED EMBODIMENTS

Figure 1B:
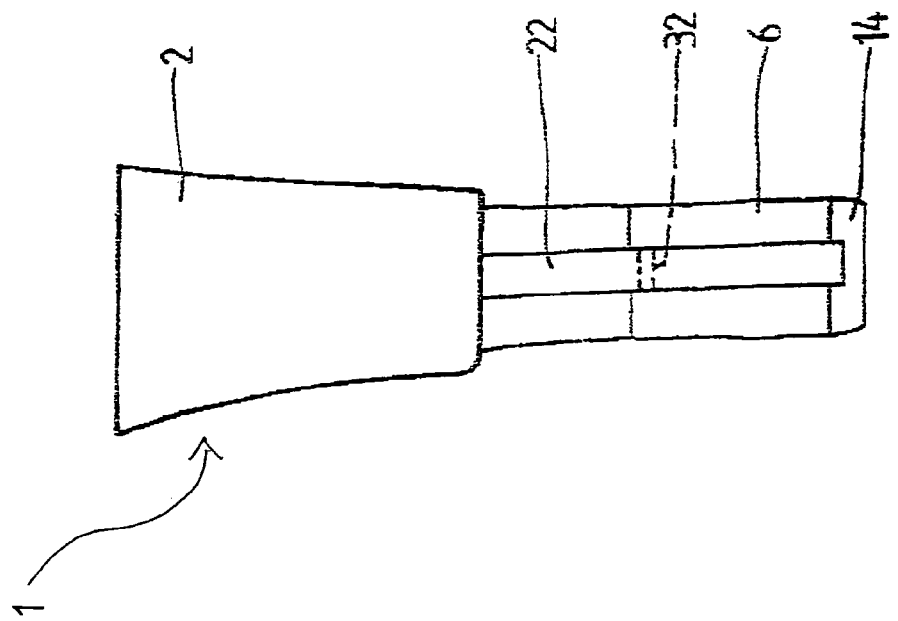
FIGS. 1a–1b are a simplified representation of a below-knee orthotic device of the invention in lateral and rear view.
Figure 1A:
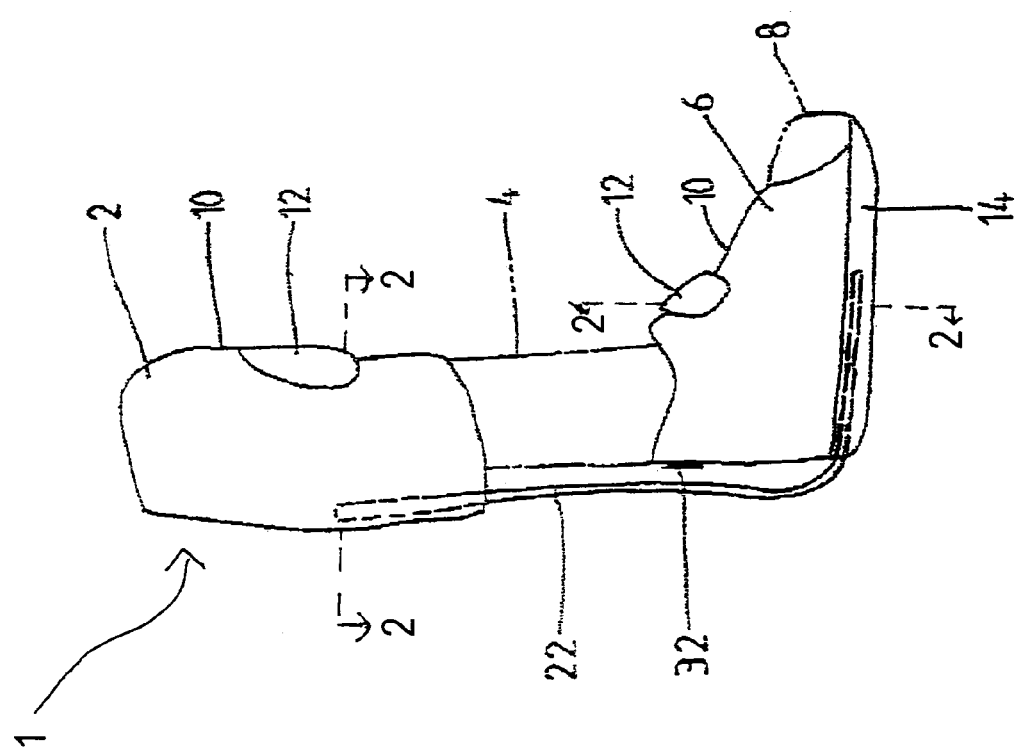

FIGS. 1a–1b show a schematic representation of a below-knee orthotic device 1 used in cases of deep paralysis for supporting the foot. By means of the orthotic device, the function of the ankle joint [talocrural articulation], i.e., lifting and lowering the foot in the longitudinal direction (forward and rearward), are to be enabled. The function of the talocalcaneonavicular joint, i.e., allowing lateral lifting and lowering, is not to be permitted by the below-knee orthotic device of the invention, i.e., the below-knee orthotic device 1 is designed to be rather stiff in the direction of movement perpendicular to the plane of the drawings of FIGS. 1a–1b.

The below-knee orthotic device 1 envelops with a lower leg sleeve 2 and the lower leg 4 (indicated in triple dots); and with a foot sleeve 6 and the foot 8 (double dots) of the patient, these sleeves being connected to each other through a support spring 22 controlling the movement.

The sleeves (2; 6) serve for transmitting the supporting forces from the support spring 22 to the leg and are preferably manufactured of plastic. For individual adaptation to the lower leg length of each patient, the lower leg sleeve 6 is adjustable in height. In accordance with FIG. 2, the sleeves (2; 6) have on their front faces an overlap 10 which may be opened for setting the below-knee orthotic device 1 in place in order to introduce the lower leg into the lower leg sleeve 2, or the foot 8 into the foot sleeve 6. The two end portions of each sleeve (2; 6), which define the overlap 10, are immobilized by a suitable closure such as a VELCRO® closure 12 extending over the two end portions of the overlap 10. In order to reduce wear, the foot sleeve 6 is provided with a sole 14. In order to enhance wearing comfort, the sleeves (2; 6) are provided with padding 20 which may, e.g., encompass the peripheral edge.

Guidance of the end portion 26 on the lower leg side on or in the lower leg sleeve 2 may be effected, for example, by application of a rib 24 surrounding the support spring 22 on the rear face of the below-knee orthotic device 1. As an alternative, the support spring 22 might also be arranged in a suitable reception formed on the below-knee orthotic device 1. In principle a different fixation is equally conceivable, such as by screws or rivets on the outer circumference of the lower leg sleeve 6, in which case an insertion groove for receiving the support spring 22 should be formed. As an alternative, the support spring 22 might also directly be secured on a shoe by the lower leg sleeve 2.

Guidance of the support spring 22 in the foot sleeve 6 in accordance with the invention is achieved such that in the resting condition, i.e. when standing, there is no contact between the rear face of the foot sleeve 6 and the heel part 30 or a support spring portion on the lower leg side. Connection between the support spring 22 and the foot sleeve 6 is achieved via the foot-side end portion 28 which preferably is embedded in the sole 14.

By means of a defined stop 32 on the rear face of the foot sleeve 6, bending of the support spring 22 in the direction of the foot sleeve 6 during initiation of a step is limited, resulting in stabilization of the initiation of a step. The stop 32 may be designed to be releasable, and then preferably is located in some kind of pocket. Fastening of the pocket may be done both on the rear face of the foot sleeve 6 and on the support spring 22. For example, when the pocket is fastened to the support spring 22, the stop 32 is releasably secured on the support spring 22 (see FIGS. 8a–8b). Fastening the stop 32 with the aid of a clamping or screwed connection is equally conceivable.

Figure 3B:
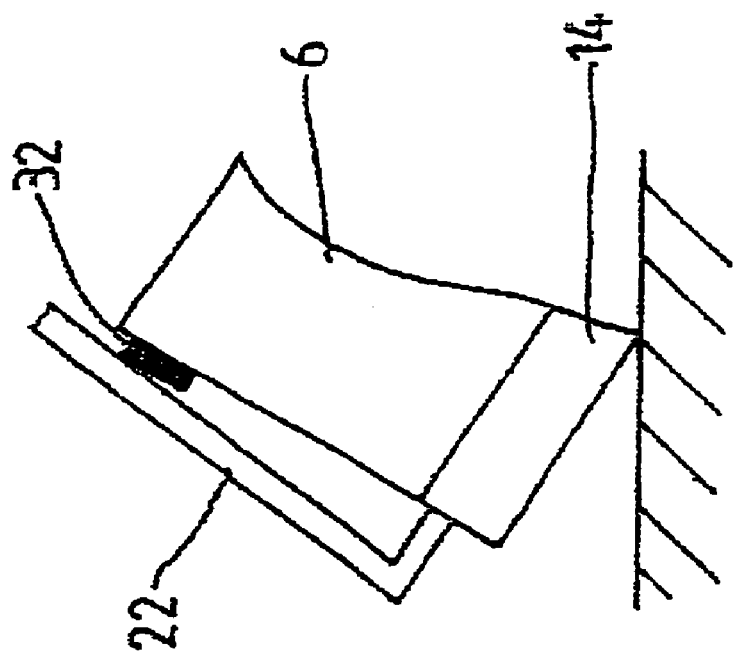
FIGS. 3a–3b are a schematic representation of the position of rest and immediately following initiation of a step.
Figure 3A:
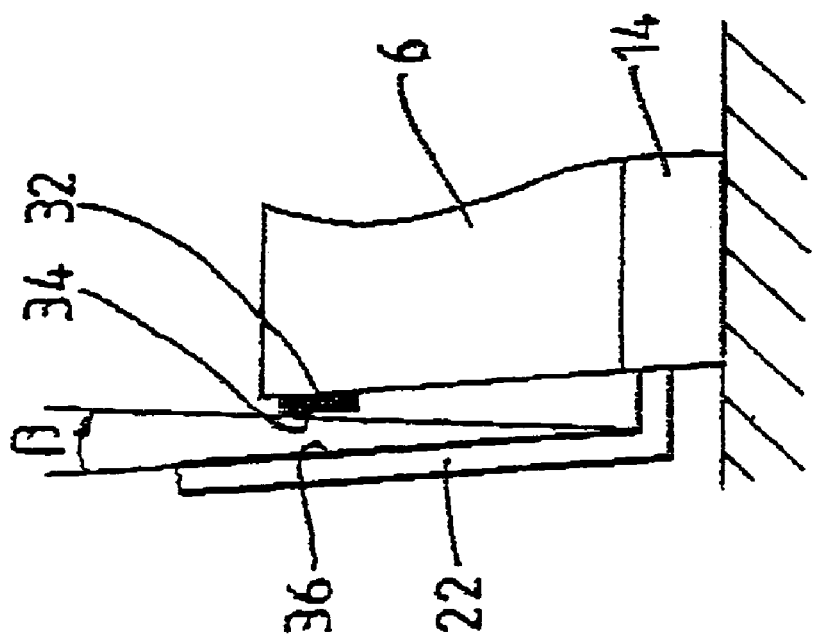

In a preferred practical embodiment in accordance with FIGS. 3a–3b, a contacting surface 36 of the support spring 22 contacts the stop surface 34 starting from an angle of $\beta \geq 5$. In accordance with the invention, the patient is thus provided with the possibility of performing pendulum movements in the walking direction of $<5°$ in the position of rest 38, without automatically starting to initiate a step. Only from pendulum movements of $\geq 5°$ the sole 14 of the foot sleeve 6 is lifted off the ground through the support spring 22 contacting the stop 32, whereby the walking process is thus initiated.

Figures 4, 5:
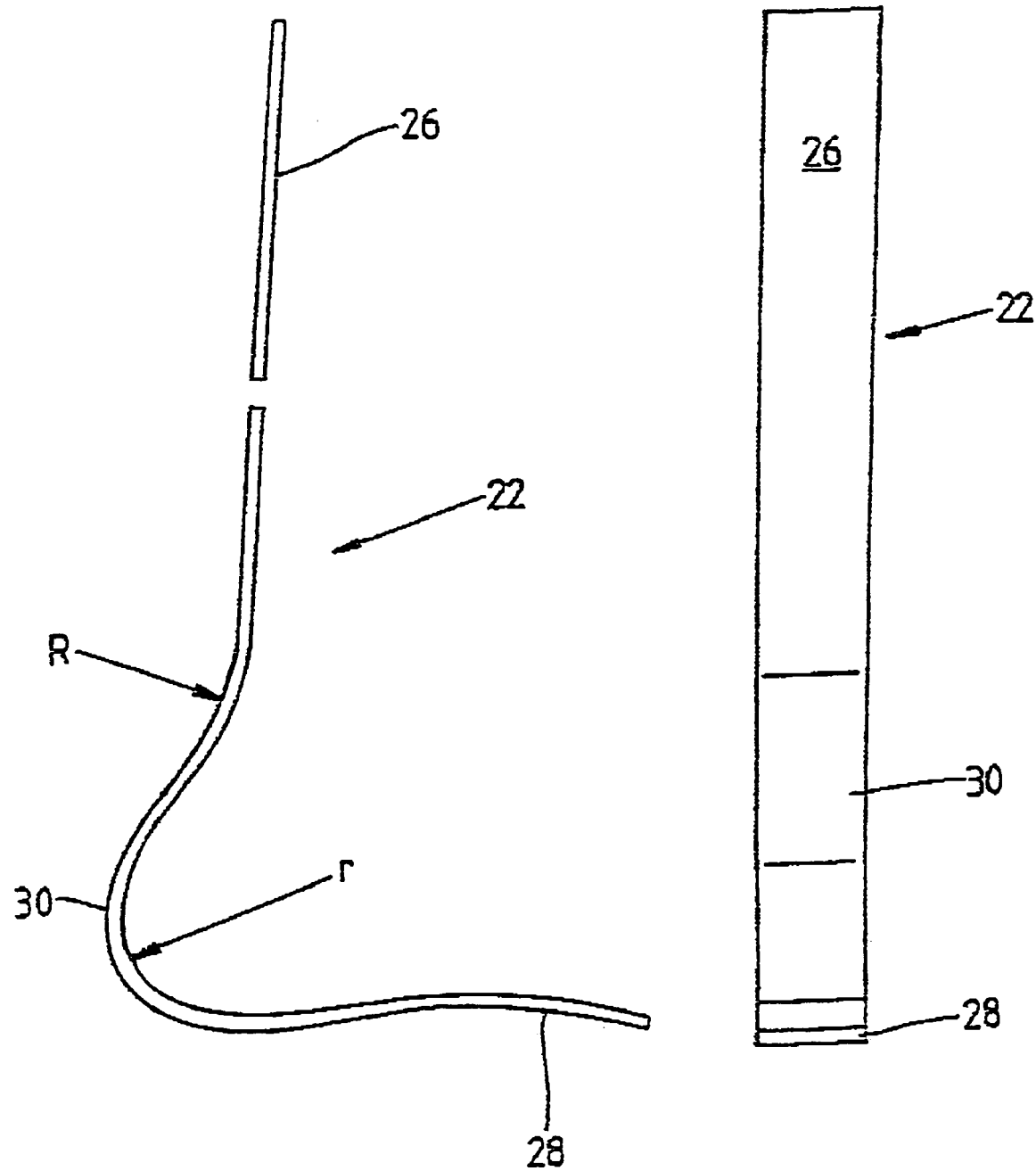
FIG. 4 is a schematic drawing of a support spring in lateral view.
FIG. 5 is a schematic drawing of a support spring in rear view.

The support spring 22 in accordance with FIG. 4 has an approximately L-shaped structure, with an end portion 26 on the lower leg side and an end portion 28 on the foot side being interconnected by a heel part 30 having a reversing curvature. The curvature of the heel part 30 is formed by two radii R and r. Radius r and the part of the support spring 22 extending as far as the lower leg sleeve essentially determine the forward mobility of the support spring 22 (on the right in FIGS. 3a–3b), whereas radius R predominantly determines rearward mobility of the support spring 22 (on the left in FIGS. 3a–3b). In other words, by suitably harmonizing radii R and r as well as the lengths of the inversely curved sections, the bending characteristics may be adapted with relative ease to the requirements of a respective patient. As a rule, the support spring 22 will be designed such that a rearward movement will only be possible in a restricted scope, whereas the forward movement should be possible through a larger angular range. Mobility is placed in the vicinity of the ankle joint.

Instead of arranging one support spring, it is also possible to arrange a plurality of springs in parallel, so that it is possible to adjust different spring rates.

As can be seen from the representation in accordance with FIG. 5, the support spring 22 has the form of a leaf spring, with fiber reinforced plastic, for example carbon fiber reinforced plastic, preferably being used as the material. This material is characterized by excellent flexural strength at minimum weight and high fatigue strength. In principle, however, it is also possible to employ other suitable materials which will nevertheless always have to be selected with a view to minimum weight and maximum fatigue strength.

FIG. 6 shows an embodiment of the stop 32 where the removable stop 32 has a wedge-shaped design, with the inclination of the stop surface 34 extending such that the foot 8, upon initiation of a step, executes a clockwise rotation about the vertical axis of the below-knee orthotic device 1 in the walking direction. Both the angle of rotation and the direction of rotation may be adjusted through no more than the inclination and the orientation of the wedge angle γ. Thanks to utilization of the stop 32 in the wedge-shaped design in accordance with the invention, sideways folding of the foot upon initiation of a step, which is particularly often observed in cases of paralysis patients, is prevented.

Moreover particular patients may in addition to the pendulum movement of $\leq 5°$ in the walking direction be given more freedom of movement in the vertical direction of rotation in the position of rest 38, e.g. with the aid of a taper of the support spring in the heel part 30, without, however, relinquishing the necessary stabilization and guidance for the foot upon initiation of a step. In other words, such a below-knee orthotic device enables a large number of degrees of freedom, whereby wearing comfort is enhanced substantially.

Figure 7A:
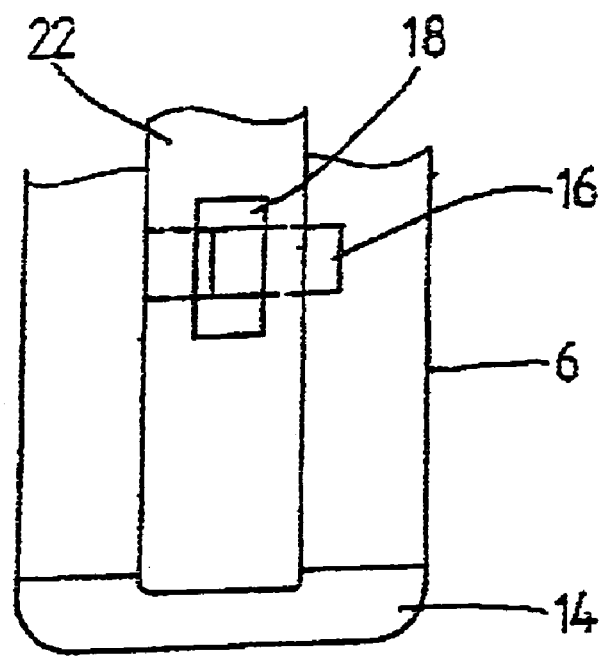
FIGS. 7a–7b are a schematic drawing of an engagement means in tongue-and-groove design.
Figure 7B:
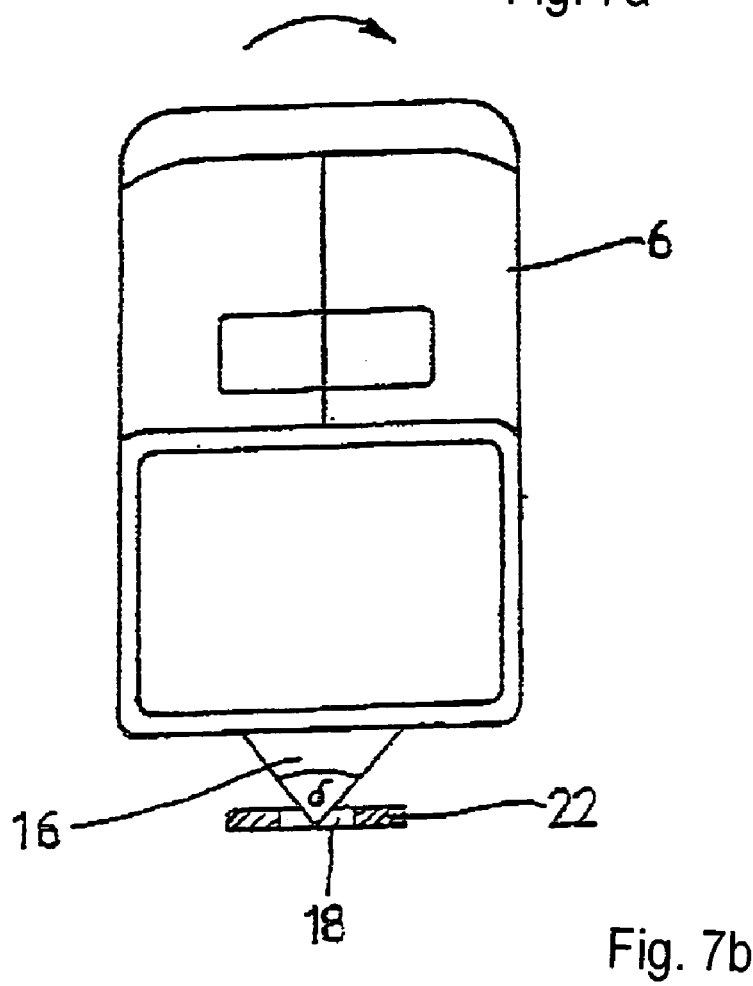

One alternative for the wedge-shaped stop 32 is represented in FIGS. 7a–7b. A wedge 16 on the rear face of the foot sleeve 6 engages a groove 18 of the support spring 22 in the heel part 30. The degree of bending of the support spring 22 and the direction of rotation may be defined through the angle of inclination 6 and the symmetry properties of the wedge 16.

The geometry of the support spring 22 is, of course, not restricted to the rectangular profile represented in FIG. 4, but it is rather also possible to employ other profiles which vary over the length of the support spring 22 so as to provide the mobility for rotation, dorsal flexion, and plantar flexion.

The use in accordance with the invention of a support spring 22 allows to return the leg into its position of rest during walking, so that the individual point of gravity will be placed in the plumb line of the body in the stationary phase even in cases of paralysis of muscle regions, perception problems, as well as for healthy persons. The support spring 22 is attached such that on the one hand secure standing is enhanced by sufficient stability, and on the other hand walking safety is achieved through sufficient flexibility (size and shape of the spring).

What is disclosed is a below-knee orthotic device in which dorsal flexion and plantar flexion are enabled by a support spring connecting a lower leg sleeve and a foot sleeve. The support spring is clamped in the foot sleeve, so that a gap is formed between the heel part and the foot sleeve, wherein bending of the support spring in stepping direction is limited through a stop on the foot sleeve.

LIST OF REFERENCE SYMBOLS 1 below-knee orthotic device
2 lower leg sleeve
4 leg
6 foot sleeve
8 foot
10 overlap
12 velcro closure
14 sole
16 wedge
18 groove
20 padding
22 support spring
24 rib
26 end portion on lower leg side
28 end portion on foot side
30 heel part
32 stop
34 stop surface
36 contacting surface
38 position of rest

The invention claimed is:

1. A below-knee orthotic device, comprising:
a lower leg sleeve adapted to envelop the lower leg;
a foot sleeve;
at least one support spring;
said lower leg sleeve hingedly connected to said foot sleeve by said support spring; and
a stop disposed on said foot sleeve;
wherein:
in a position of rest, a gap is formed between a portion of said foot sleeve and a portion of said support spring;
in a stepping direction, bending of said support spring is limited by contacting said stop; and
said stop is releasably secured with a rear face of said foot sleeve or on said support spring.

2. The below-knee orthotic device in accordance with claim 1, wherein in the position of rest, there is no contact between a heel part or a part of said support spring on a lower leg side and a rear face of said foot sleeve.

3. The below-knee orthotic device in accordance with claim 1, wherein a surface of said stop is set to be parallel with, or inclined relative to a contacting surface of said support spring when said stop and said support spring enter into contact with each other.

4. The below-knee orthotic device in accordance with claim 3, wherein said stop is a wedge.

5. The below-knee orthotic device in accordance with claim 4, wherein said support spring contacts said stop starting from an angle $\beta \geq 5°$.

6. The below-knee orthotic device in accordance with claim 1, wherein said support spring includes a reversing curvature in a heel part and two end portions, the heel part and the two end portions support a lower leg rear side or a sole of the foot in a longitudinal and/or transverse direction.

7. The below-knee orthotic device in accordance with claim 1, wherein said support spring is connected with said foot sleeve via an end portion on a foot side of said support spring.

8. The below-knee orthotic device in accordance with claim 1, wherein said lower leg sleeve is adjustable in height.

9. The below-knee orthotic device in accordance with claim 1, wherein said support spring is a leaf spring.

10. The below-knee orthotic device in accordance with claim 1, wherein said support spring is a leaf spring made of fiber reinforced plastic.

11. The below-knee orthotic device in accordance with claim 1, further comprising a releasable engagement means whereby said support spring and said foot sleeve are releasably connected from a predetermined inclination angle $\delta$.

12. The below-knee orthotic device in accordance with claim 10, wherein said leaf spring is made of carbon fiber reinforced plastic.

13. The below-knee orthotic device in accordance with claim 1, wherein said support spring contacts said stop starting from an angle $\beta \geq 5°$.

14. The below-knee orthotic device in accordance with claim 1, wherein said stop is disposed on said support spring.

* * * * *

UNITED STATES PATENT AND TRADEMARK OFFICE
CERTIFICATE OF CORRECTION

| | |
|---|---|
| PATENT NO. | : 7,112,180 B2 |
| APPLICATION NO. | : 10/478650 |
| DATED | : September 26, 2006 |
| INVENTOR(S) | : Norbert G. Guenther |

It is certified that error appears in the above-identified patent and that said Letters Patent is hereby corrected as shown below:

Col. 1, lines 43-47: this paragraph was erroneously duplicated and added by the Patent Office. This paragraph correctly begins on col. 3, line 7;

Col. 2, line 1: "walking up-and" should be --walking up- and--;

Col. 3, line 57: "22. the stop" should be --22, the stop--;

Col. 4, line 63: "inclination 6" should be --inclination δ--.

Col. 3, line 7: insert paragraph from col. 1, lines 43-47, beginning with "The" and ending with, "movement".

Signed and Sealed this

Thirteenth Day of February, 2007

JON W. DUDAS
*Director of the United States Patent and Trademark Office*